United States Patent
Wu et al.

(10) Patent No.: US 8,674,070 B2
(45) Date of Patent: *Mar. 18, 2014

(54) CANCER-TARGETING PEPTIDES AND USES THEREOF IN CANCER THERAPY

(75) Inventors: Han-Chung Wu, Taipei (TW); Chien-Yu Chiu, Taipei (TW)

(73) Assignee: Academia Sinica, Taipei (TW)

( * ) Notice: Subject to any disclaimer, the term of this patent is extended or adjusted under 35 U.S.C. 154(b) by 24 days.

This patent is subject to a terminal disclaimer.

(21) Appl. No.: 13/201,749

(22) PCT Filed: Feb. 19, 2010

(86) PCT No.: PCT/US2010/024646
§ 371 (c)(1),
(2), (4) Date: Oct. 25, 2011

(87) PCT Pub. No.: WO2010/096603
PCT Pub. Date: Aug. 26, 2010

(65) Prior Publication Data
US 2012/0039988 A1    Feb. 16, 2012

Related U.S. Application Data

(60) Provisional application No. 61/153,725, filed on Feb. 19, 2009.

(51) Int. Cl.
*A61K 38/04*  (2006.01)
*A61K 38/10*  (2006.01)
*A61K 38/00*  (2006.01)

(52) U.S. Cl.
USPC .......................... 530/327; 514/19.2; 514/19.3

(58) Field of Classification Search
None
See application file for complete search history.

(56) References Cited

U.S. PATENT DOCUMENTS

2003/0049262 A1    3/2003   Love et al.
2003/0232762 A1   12/2003   Ruoslahti et al.

OTHER PUBLICATIONS

Aina, O.H. et al.; Molecular Pharmaceutics, vol. 4(5):631-651 (2007).
Aina, O.H. et al.; Biopolymers, vol. 66:184-199 (2002).
Singh et al.; Cancer Research, vol. 67(2):626-633 (2007).

*Primary Examiner* — Joseph Woitach
*Assistant Examiner* — Kimberly A Aron
(74) *Attorney, Agent, or Firm* — Cesari and McKenna, LLP

(57) ABSTRACT

Cancer-targeting peptides and uses thereof in cancer therapy.

17 Claims, 4 Drawing Sheets

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial
<220> FEATURE:
<223> OTHER INFORMATION: Synthetic peptide

<400> SEQUENCE: 1

Gln Asn Ile Tyr Ala Gly Val Pro Met Ile Ser Phe
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic peptide
```

```
<400> SEQUENCE: 2

Glu Ala Thr Asn Ser His Gly Ser Arg Thr Met Gly
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic peptide

<400> SEQUENCE: 3

Thr Val Ser Trp Ser Thr Thr Gly Arg Ile Pro Leu
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic peptide

<400> SEQUENCE: 4

Gln Leu Glu Phe Tyr Thr Gln Leu Ala His Leu Ile
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic peptide

<400> SEQUENCE: 5

Ser Met Asp Pro Phe Leu Phe Gln Leu Leu Gln Leu
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic peptide

<400> SEQUENCE: 6

Arg Leu Leu Asp Thr Asn Arg Pro Leu Leu Pro Tyr
1               5                   10
```

CANCER-TARGETING PEPTIDES AND USES THEREOF IN CANCER THERAPY

RELATED APPLICATION

This application is the national phase application of International Application No. PCT/US2010/024646, filed on Feb. 19, 2010, which claims priority to U.S. Provisional Application No. 61/153,725, filed on Feb. 19, 2009, the content of which is hereby incorporated by reference in its entirety.

BACKGROUND OF THE INVENTION

Targeted drug delivery significantly improves efficacy of cancer therapy. The key to accomplishing this mission is to identify agents that specifically target cancer cells.

SUMMARY OF THE INVENTION

The present invention is based on the unexpected discovery that a number of peptides, including QNIYAGVPMISF (SEQ ID NO:1), EATNSHGSRTMG (SEQ ID NO:2), TVSWSTTGRIPL (SEQ ID NO:3), QLEFYTQLAHLI (SEQ ID NO:4), and SMDPFLFQLLQL (SEQ ID NO:5), specifically target breast cancer cells, thereby facilitating drug delivery to breast tumor sites.

Accordingly, one aspect of this invention features a breast cancer-targeting peptide including one of the amino acid sequences SEQ ID NOs:1-5. Any of these peptides can be conjugated with an anti-cancer drug for breast cancer treatment. In one example, the anti-breast cancer drug is encapsulated in a microparticle (e.g., a liposome). Exemplary anti-cancer drugs include, but are not limited to, doxorubicin, tamoxifen, vinorelbine, vincristine, paclitaxel, lurtotecan, docetaxel, adriamycin, epirubicin, mitoxantrone, mitomycin, gemcitabine, cisplatin, oxaliplatin, vinblastine, 5-FU, UFUR, anastrozole, letrozole, and exemestane.

Another aspect of this invention features a targeted drug delivery method by administering to a subject having breast cancer (e.g., a human breast cancer patient) an effective amount of a conjugate containing one of the breast cancer-targeting peptides described above and an anti-cancer drug. "An effective amount" as used herein refers to the amount of the conjugate for delivering each active agent included therein to a solid tumor site so that the active agent confers therapeutic effect on the subject, either alone or in combination with one or more other active agents. Effective amounts vary, as recognized by those skilled in the art, depending on route of administration, excipient choice, and co-usage with other active agents.

Also within the scope of this invention is use of any of the conjugates described above for breast cancer treatment or for the manufacture of a medicament used in treating breast cancer.

The details of one or more examples of the invention are set forth in the description below. Other features or advantages of the present invention will be apparent from the following detailed description of several embodiments, and also from the appended claims.

BRIEF DESCRIPTION OF THE DRAWINGS

The drawings are first described.

DETAILED DESCRIPTION OF THE INVENTION

Figure 1:
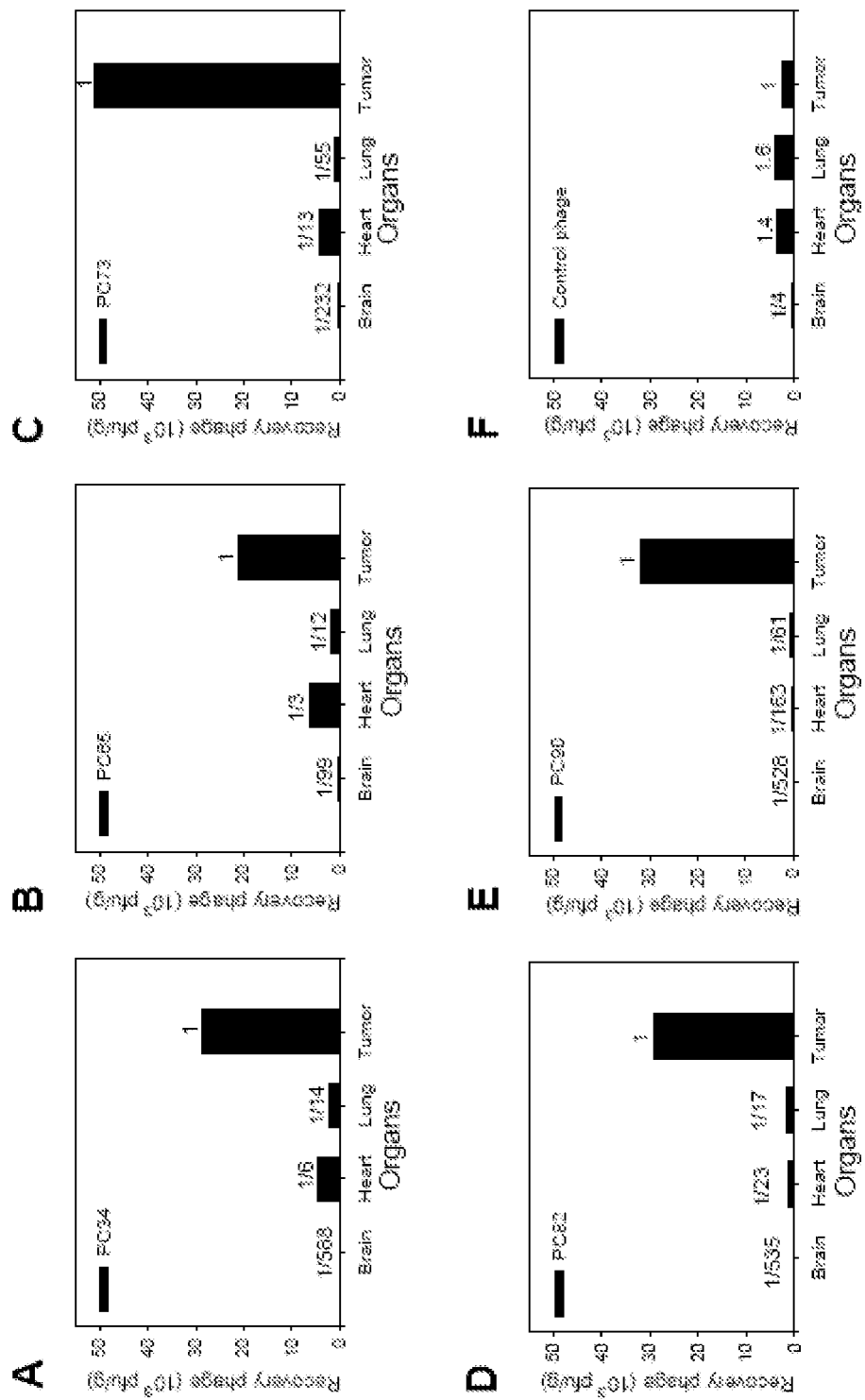
FIG. 1 is a diagram showing specific binding activities of cancer-targeting peptides, expressed on phage surfaces, to breast tumor xenografts. Panel A: phage clone PC34, displaying a peptide having the amino acid sequence of SEQ ID NO:1. Panel B: phage clone PC65, displaying a peptide having the amino acid sequence of SEQ ID NO:2. Panel C: phage clone PC73, displaying a peptide having the amino acid sequence of SEQ ID NO:3. Panel D: phage clone PC83, displaying a peptide having the amino acid sequence of SEQ ID NO:4. Panel E: phage clone PC90, displaying a peptide having the amino acid sequence of SEQ ID NO:5. Panel F: control phage clone PC34, displaying a control peptide.

The present invention relates to a number of breast cancer-targeting peptides, i.e., a peptide including one of the amino acid sequences SEQ ID NOs:1-5. The term "peptide" used herein refers to a polymer composed of up to 100 amino acid monomers via peptide bond linkage. Each of the breast cancer-targeting peptides described herein can include up to 50 (e.g., 30) amino acids. These peptides can be prepared by conventional methods, i.e., chemical synthesis or recombinant technology.

When necessary, any of the breast cancer-targeting peptides described herein can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with NaBH$_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with NABH$_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

As shown in Examples 1-3 below, the breast cancer-targeting peptides described herein particularly bind to breast cancer tissues/cells, both in vivo and in vitro. Thus, when conjugated with an anti-cancer drug, they direct the drug to a breast cancer site, thereby facilitating breast cancer treatment. As used in this disclosure, "conjugated" means two entities (here a breast cancer targeting peptide and an anti-cancer drug) are associated with sufficient affinity that the therapeutic benefit of the association between the two entities is realized. Conjugation can be achieved by covalent or noncovalent bonding, as well as by other forms of association, such as entrapment of one entity on or within the other, or of either or both entities on or within a third entity (e.g., a micelle).

In one example, one of the breast cancer-targeting peptides described herein is covalently linked, directly or indirectly, to an anti-cancer drug to form a treatment conjugate via conventional methods. The drug can be a chemotherapy agent, such as drugs that stop DNA building block synthesis (e.g., methotrexate, fluorouracil, hydroxyurea, and mercaptopurine), drugs that directly damage DNA (e.g., cisplatin, daunorubicin, doxorubicin, and etoposide), drugs that affect mitotic spindle synthesis or breakdown (e.g., vinblastine, vincristine, and pacitaxel), or drugs that disrupt angiogenesis (e.g., anti-VEGF antibody, angiostatin, endostatin, and tumstatin). Alternatively, the anti-breast cancer drug can be a radiotherapy agent (e.g., $^{90}$Y, $^{125}$I, $^{188}$Re, $^{111}$In DTPA, or $^{131}$I Sodium iodide).

In another example, the breast cancer-targeting peptide is linked to a vehicle molecule (i.e., a microparticle), which encapsulates the anti-breast cancer drug, so as to form a treatment conjugate. Vehicle molecules include micelle, liposome (e.g., cationic liposome), nanoparticle, microsphere, or biodegradable polymer. A breast cancer-targeting peptide can be tethered to the vehicle molecule by a variety of linkages (e.g., a disulfide linkage, an acid labile linkage, a peptide-based linkage, an oxyamino linkage, or a hydrazine linkage). The anti-breast cancer drug encapsulated within the vehicle can be associated with lipophilic molecules, which can aid in the delivery of the imaging molecule/anti-tumor drug to the interior of the vehicle.

In a preferred example, a breast cancer-targeting peptide is linked to a liposome that encapsulates an anti-cancer drug to be delivered to a tumor site. The term "liposome" refers to vesicles comprised of one or more concentrically ordered lipid bilayers, which encapsulate an aqueous phase. The aqueous phase typically contains the compound to be delivered to a tumor site. Upon reaching a tumor site, the liposome fuses with the plasma membranes of local tumor cells or tumor blood vessel cells, thereby releasing the compound into the cytosol. Alternatively, the liposome is endocytosed or otherwise taken in by the tumor cells or of tumor blood vessel cells as the content of a transport vesicle (e.g., an endosome or phagosome). Once in the transport vesicle, the liposome either degrades or fuses with the membrane of the vesicle and releases its contents. Liposome membranes can be constructed so that they become destabilized when the nearby environment becomes acidic (see, e.g., PNAS 84:7851, 1987; Biochemistry 28:908, 1989). When liposomes enter a target cell, they become destabilized and release their encapsulated contents. This destabilization is termed fusogenesis. Dioleoylphosphatidylethanolamine (DOPE) is commonly used to facilitate this process.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

Any of the breast cancer treatment conjugates described herein can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

To use any of the conjugates described herein for tumor treatment, the conjugate can be administered orally, parenterally, topically, rectally, nasally, buccally, vaginally, via an implanted reservoir, or via inhalation spray. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets/capsules for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An oxadiazole compound-containing composition can also be administered in the form of suppositories for rectal administration.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Binding of Cancer-Targeting Peptides Expressed on Surface of Phage Particles

BT483 cells (breast cancer cells) and human mucosal epithelial cells (normal cells) were seeded in a 96-well plate, following the procedures described in Lo et al., Mol. Cancer Ther 7:579-589 (2008) and Lee et al., Cancer Res. 64:8002-8008 (2004). These cells were incubated with both a control helper phage that is inactivated by ultraviolet and one of the five test phages listed below, each expressing one of the five peptides also listed below:

| Phage Clones | Peptide Displayed |
|---|---|
| PC34: | QNIYAGVPMISF (SEQ ID NO: 1) |
| PC65: | EATNSHGSRTMG (SEQ ID NO: 2) |
| PC73: | TVSWSTTGRIPL (SEQ ID NO: 3) |
| PC82: | QLEFYTQLAHLI (SEQ ID NO: 4) |
| PC90: | SMDPFLFQLLQL (SEQ ID NO: 5) |

After several rounds of wash to remove unbound phage particles, the cells were further incubated with horseradish peroxidase (HRP) conjugated anti-M13 monoclonal antibody (Pharmacia, Uppsala, Sweden) and then with o-phenylenediamine dihydrochloride (sigma, MO, USA), a substrate of peroxidase. The cells were washed again and analyzed in an ELISA reader to measure the optical density at 490 nm in each well. The $OD_{490}$ values indicate the binding activity of the test phages to the breast cancer cells and to the normal cells. All of the five test phages exhibited significantly higher binding activities to the breast cancer cells than to the normal cells, indicating that the five peptides expressed thereon target cancer cells but not normal cells.

The binding activities of the five test phages to the breast cancer cells and to the normal cells were also determined by flow cytometry as follows. The cells were harvested and suspended in PBS containing 50 mM EDTA and then incubated with one of the five test phages. After washing, the cells were incubated with the anti-M13 antibody mentioned above and then with a FITC-conjugated goat anti-mouse IgG antibody. The cells were washed again and analyzed by a flow cytometer (Becton Dickinson). The results thus obtained show that the percentages of the test phage-bound cancer cells were significantly higher than those of the test phage-bound normal cells, indicating that all of the five peptides expressed on the test phages specifically bound to breast cancer cells.

EXAMPLE 2

In Vivo Binding Activity of Test Phages to Cancer Tissues and Normal Organs

SCID mice were injected subcutaneously (s.c.) in the dorsolateral flank with $1 \times 10^7$ BT483 cells to induce breast cancer xenografts. The mice bearing xenograft tumors at a size of around 300 mm$^3$ were administered intravenously (i.v.) with one of the five test phages mentioned in Example 1 above ($10^9$ pfu) or a control phage. After perfusion, xenograft tumors and organs (i.e., brain, heart, and lung) were removed from each mouse and homogenized. The phages bound to each tissue sample were eluted, recovered using ER2738 bacterial cells as the host, and titered on IPTG/X-Gal agar plates, following the methods described in Lee et al., Cancer Res. 67:10958-10965 (2007) and Lo et al., Mol. Cancer. Ther 7:579-589 (2008).

As shown in FIG. 1, the recovery rates of phage clones PC34, PC65, PC73, PC82 and PC90 from tumor tissues were much higher than those from normal organs, including the brain, heart, and lung, indicating that all of the five phage clones homed to tumor mass, but not normal organs. More specifically, the concentrations of the phages homed to the tumor mass were 3.0 to 588 fold higher that those of the phages homed to the normal organs. The control phage targeted neither the tumor xenografts nor the normal organs.

EXAMPLE 3

Cancer Targeting Activity of Peptide SMDPFLFQLLQL (SEQ ID NO:5)

The in vitro cancer targeting activity of phage clone PC90, expressing peptide SMDPFLFQLLQL (SEQ ID NO:5), was tested as follows. Fresh breast cancer tissue samples were obtained from twenty patients having mammary infiltrating ducal carcinoma. Each of the tissue samples was sliced to 4 μm and fixed in 1% paraformaldehyde. The sliced tissue samples were then incubated with PC90 or a control phage. After being washed by PBS containing 1% Tween 20 ($PBST_{0.1}$), the samples were incubated with an anti-M13 mouse mAb (Amersham Biosciences, Piscataway, N.J., USA) for 1 hour at room temperature, washed again with $PBST_{0.1}$, and the immunoreactivity of each sample was determined using a biotin-free super sensitive polymer-HRP detection system (Biogenex, San Ramon, Calif., USA), following the procedures described in Lee et al. (2004) and Lo et al. The slides, to which the tissue samples were attached, were counterstained with hematoxylin, mounted with Aquatex (Merck, Dannstadt, Germany), and examined by light microscopy. The percentage of the positively stained cells was determined following a method described in Hall et al., J. Pathol. 172:1-4 (1994). In this study, PC90, but not the control phage, was found to target the tumor cells in the tissue samples.

The cancer targeting activity of PC90 was confirmed by a peptide competition assay, in which the cancer tissue samples were incubated with (1) the synthetic peptide (100 ng/ml) SMDPFLFQLLQL (SEQ ID NO:5) (SP90) and PC90 ($10^9$ pfu) or (2) the control peptide (100 ng/ml) RLLDTNR-PLLPY (SEQ ID NO:6; see Lee et al., cancer Res. 64:8002-8008, 2004) and PC90. SP90 and the control peptide were synthesized and purified by reverse-phase high-performance liquid chromatography. The resultant peptides, having a purity of greater than 95%, were conjugated, if necessary, with FITC or biotin at their N-termini.

The results obtained from this study showed that SP90, but not the control peptide, competed against PC90 for binding to the cancer cells in the tissue samples.

Next, the in vivo cancer targeting activity of PC90 was tested in breast tumor-bearing SCID mice following the method described in Example 2 above. The results showed that PC90 particles were bound to cancer cells in the tumor xenografts but not to normal organs, including the brain, heart, and lung.

SP90 was co-administered to test its ability of blocking PC90 from binding to the tumor tissues. Briefly, 100 µg SP90 or the control peptides described above were co-injected with PC90 to mice bearing breast tumor xenografts. The normal organs and tumor tissues were removed and fixed in Bouin's solution (Sigma, Mo., USA). After fixation, the samples were embedded in paraffin blocks, sliced to sections, and the sections were deparaffinized, rehydrated, and subjected to immunostaining using the mouse anti-M13 mAb described in Example 1 above. SP90 significantly inhibited PC90 from binding to tumor tissues. More specifically, 100 µg SP90 inhibited 97% of PC90 from binding to the tumor tissues while the control peptide did not exhibit any inhibitory activity.

Taken together, the results discussed above indicate that peptide SMDPFLFQLLQL (SEQ ID NO:5), either in synthetic form or being expressed on the surface of a phage, specifically target breast cancer cells.

EXAMPLE 4

Targeted Treatment of Breast Cancer with Peptide SMDPFLFQLLQL Conjugated Liposomes Encapsulating Doxorubicin Preparation of Peptide-Conjugated Doxorubicin-Encapsulated Liposomes Peptide-conjugated liposomes containing doxorubicin were prepared as described in Lee et al. (2007), Lo et al, and Lee et al. (2004). Briefly, the peptide was coupled to NHS-PEG-DSPE [N-hydroxysuccinimido-carboxyl-polyethylene glycol (MW, 3400)-derived distearoylphosphatidyl ethanolamine] (NOF Corporation, Japan) in a 1:1.5 molar ratio. The reaction was completed and confirmed by quantifying the non-reacted amino groups using TNBS (Trinitrobenzenesulfonate) (Sigma, Mo., USA). Doxorubicin was encapsulated by liposomes at a ratio of 1 mg of drug per 10 µmol phospholipids. Peptidyl-PEG-DSPE was then conjugated to the doxorubicin-encapsulated liposomes after co-incubation at a transition temperature of the lipid bilayer. Each of the resultant peptide-conjugated liposomes contained around 500 peptide molecules as determined by the method described in Kirpotin, et al., Biochemstry, 36: 66-75 (1997). Following this method, a SP90-conjugated doxorubicin-encapsulated liposome (SP-LD) and a control peptide-conjugated doxorubicin-encapsulated liposome (CP-LD) were prepared.

In Vitro Endocytosis of Doxorubicin Mediated by SP-LD

BT483 cells were incubated with SP-LD or CP-LD at 37° C. for five minutes. The cells were then washed with PBS, fixed, and examined under an electron microscope to detect internalization of the liposomes in cell endosomes. The results indicate that in the cells incubated with SP-LD, the liposomes were found to be internalized into around 90% of their endosomes, while in the cells incubated with CP-LD, only around 51% of their endosomes were found liposome positive. This indicates that SP-LD mediated liposome endocytosis by the breast cancer cells.

Treating Breast Tumor with SP-LD

SCID mice (4-6 weeks of age) were injected s.c. in the dorsolateral flank with $1 \times 10^7$ BT483 cells to induce breast cancer xenografts. The tumor volumes in these mice were determined by the formula: length×(width)×0.52. The mice bearing xenograft tumors at a size of around 50-100 mm$^3$ were randomly assigned to four groups, each of which was treated as follows via administration through their tail veins.

Group 1: treated with SP90 conjugated doxorubicin-containing liposomes (SP90-LD) at a doxorubicin dosage of 3 mg/kg, once a week for three weeks, Group 2: treated with doxorubicin-containing liposomes (LD), at a doxorubicin dosage of 3 mg/kg, once a week for three weeks, Group 3: treated with free doxorubicin (FD), at a doxorubicin dosage of 3 mg/kg, once a week for three weeks, and Group 4: treated with saline once a week for three weeks (blank control).

Mouse body weights and tumor sizes were measured twice a week. Tumor volumes were calculated following the formula described above.

Figure 2:
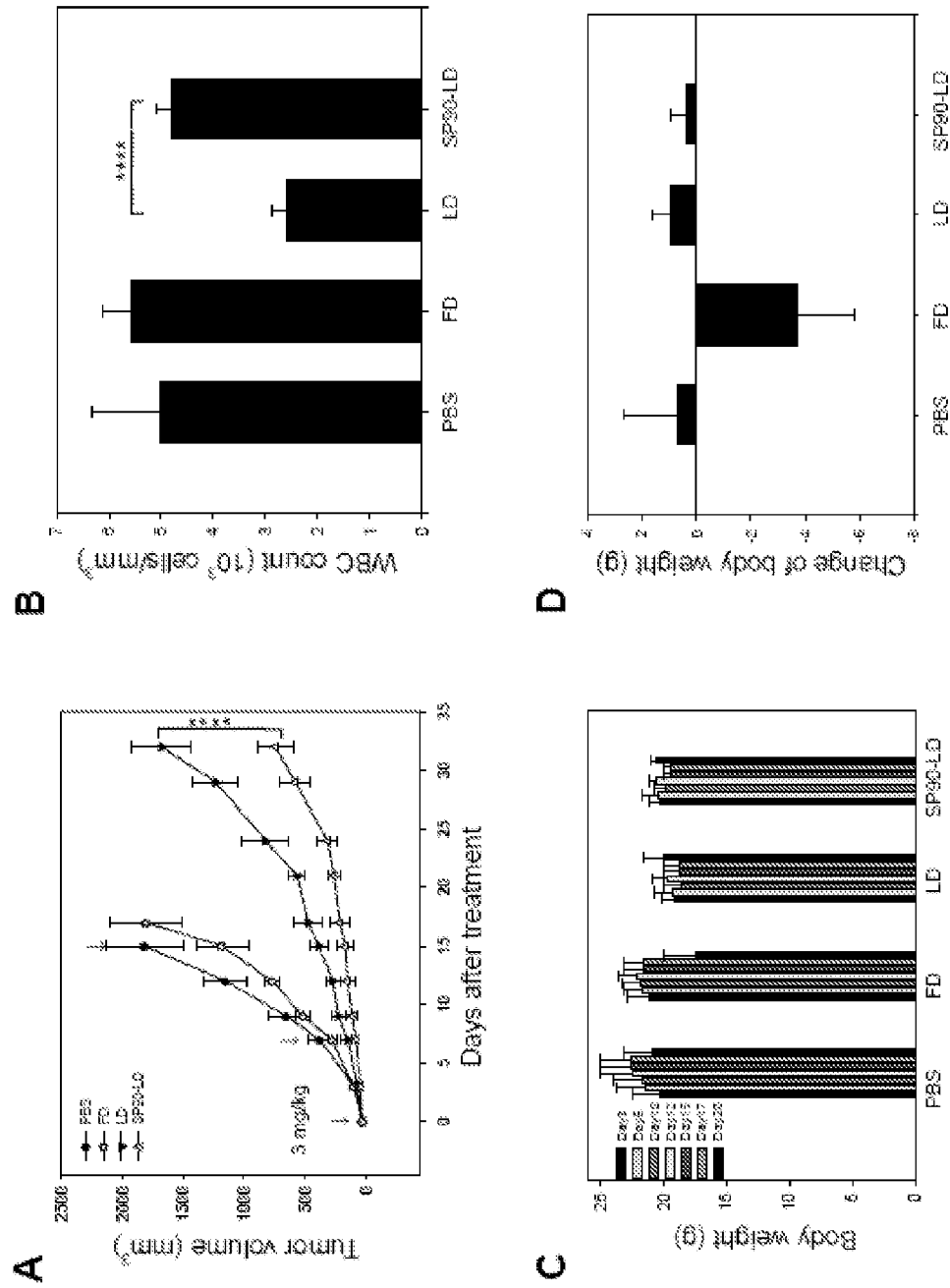
FIG. 2 is a diagram showing anti-breast tumor activities of free doxorubicin (FD), doxorubicin encapsulated in liposome (LD), and doxorubicin encapsulated in SP90-conjugated liposome (SP90-LD). SP90 refers to the peptide displayed on phage clone PC90 (SEQ ID NO:5). Panel A: tumor volumes in breast tumor-bearing mice treated with FD, LD, or SP90-LD. Panel B: white blood cell (WBC) counts in breast tumor-bearing mice treated with FD, LD, or SP90-LD. Panel C: body weights in breast tumor-bearing mice treated with FD, LD, or SP90-LD. Panel D: changes in body weights in breast tumor-bearing mice treated with FD, LD, or SP90-LD.

As shown in FIG. 2, Panel A, the average tumor volume of the Group 2 mice (treated with LD) was around 2.2 fold larger than that of the Group 1 mice (treated with SP90-LD) (n=6, $P<0.01$). The average tumor volumes of the Group 3 mice (treated with FD) and the control mice were 8.3 fold and 15.4 fold larger than that of the Group 2 mice, respectively (n=6, $P<0.005$).

The total white blood cell (WBC) numbers in the treated mice were determined three days after the last treatment (i.e., on day 17) as follows. The blood was drawn from the submaxillary vein of each mouse and mixed gently with 15% EDTA solution to prevent coagulation. The blood was then mixed with a red blood cell lysis buffer containing 2% acetic acid and 1% of Gentian violet (Sigma-Aldrich, Saint Louis, Mo., USA) and incubated at room temperature. The number of the WBCs was countered using a hemacytometer.

The total number of the WBCs of the SP90-LD-treated mice was $4.8 \times 10^3/mm^3$, which was similar to that of the control mice ($5.0 \times 10^3/mm^3$) and the FD-treated mice ($5.6 \times 10^3/mm^3$) but much higher than that of the LD-treated mice ($2.6 \times 10^3/mm^3$). See FIG. 2, Panel B. This data indicates that SP-90-LD is less toxic than LD.

The results obtained from this study also indicate that no significant body weight loss was observed in the Groups 1, 2, and 4, indicating that, like saline and LD, SP90-LD also did not cause body weight loss. See FIG. 2, Panels C and D.

Figure 3:
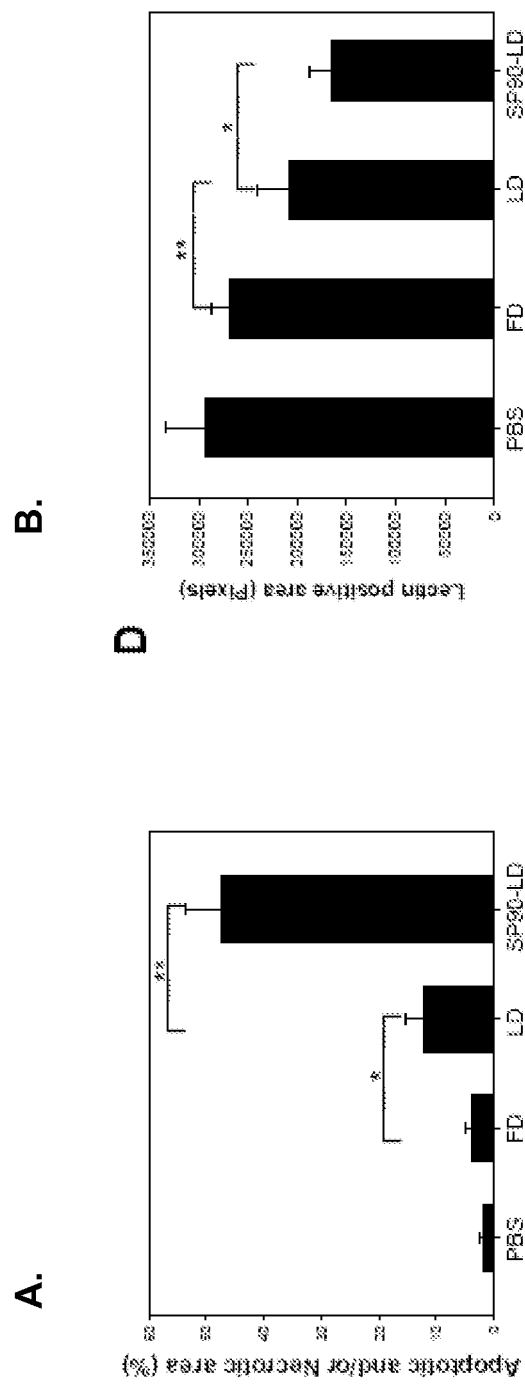
FIG. 3 is a diagram showing necrotic/apoptotic areas in breast tumor-bearing mice treated with FD, LD, or SP90-LD. Panel A: apoptotic and necrotic areas. Panel B: lectin positive areas (indicating presence of tumor blood vessels).

The histopathology of the tumor tissues in the treated mice was examined by H&E staining as follows. The tumor tissues, frozen and sectioned, were incubated with terminal deoxynucleotidyl transferase-mediated dUTP nick end labeling reaction mixture (Roche Diagnostics, Switzerland) at 37° C. for one hour to detect necrotic/apoptotic areas. The slides, to which the tissue samples were attached, were counterstained with mounting medium with DAPI (Vector Laboratories). The slides were then visualized under a fluorescent microscope and analyzed with MetaMorph software (Molecular Devices, PA, USA). Markedly disseminated necrotic/apoptotic areas were present throughout the whole section of SP90-LD treated mice, while in the LD treated mice, fewer necrotic/apoptotic areas were found. The mice treated with FD and the control mice showed even less necrotic/apoptotic areas. See FIG. 3, Panel A. These results indicate that SP90-LD is more efficient in inducing tumor cell necrosis/apoptosis than LD and FD.

The effect of SP90-LD on tumor blood vessel formation was also examined. Tumor tissues were removed from the treated mice, fixed with 4% paraformaldehyde and embedded with paraffin. Blood vessels in the tumor tissues were detected by staining with *Lycopersicon esculentum* (tomato) lectin conjugated to biotin (Vector, CA, USA) and then with streptavidin-conjugated rhodamine (Pierce, Ill., USA). In the SP90-LD-treated mice, the number of tumor vessels was significantly less than that in the LD-treated mice. See FIG. 3, Panel B. The mice treated with FD the control mice showed high tumor vascular density. These results demonstrate that SP90-LD is more effective in inhibiting tumor angiogenesis than LD and FD.

Finally, doxorubicin localization in the treated mice was examined. Briefly, three groups of SCID mice bearing breast cancer xenografts (~300 mm$^3$) were injected with SP90-LD, LD, or FD at a dose of 2 mg/kg through their tail vein. At selected time points, three mice in each group were anaesthetized and sacrificed. Blood samples were collected via submaxillary punctures, and plasma samples were prepared therefrom. After perfusion, the tumor xenografts and normal organs (i.e., brain, heart, and lung) were removed and homogenized. See Mayer et al., J. Pharmacol. Exp. Ther. 280:1406-1414 (1997). These tissues samples were analyzed by spectrofluorometry at $\lambda_{ex}$ 485/20 nm and $\lambda_{em}$ 645/40 nm (Synergy HT Multi-Detection Microplate Reader, BioTek Instruments, Winooski, Vt. 05404 USA). The data thus obtained were normalized against the data obtained from mice not treated with doxorubicin. A standard doxorubicin curve was prepared following the same procedures described above using control homogenates that contain doxorubicin at a series of pre-determined levels. The doxorubicin levels (μg) in the tissue samples were determined based on the standard curve. The doxorubicin tissue concentration refers doxorubicin level per milliliter of plasma or per gram of tissue.

Tissue localization of doxorubicin was also examined by detecting its autofluorescence using a Zeiss Axiovert 200M inverted microscope having a 100 W HBO mercury light source equipped with a 546/12 nm excitation and a 590 nm emission filter set. Tissue sections were observed under a FLUAR 10x/0.50 NA lens and the images were captured using a Roper Scientific CoolSnap HQ CCD camera.

Figure 4:
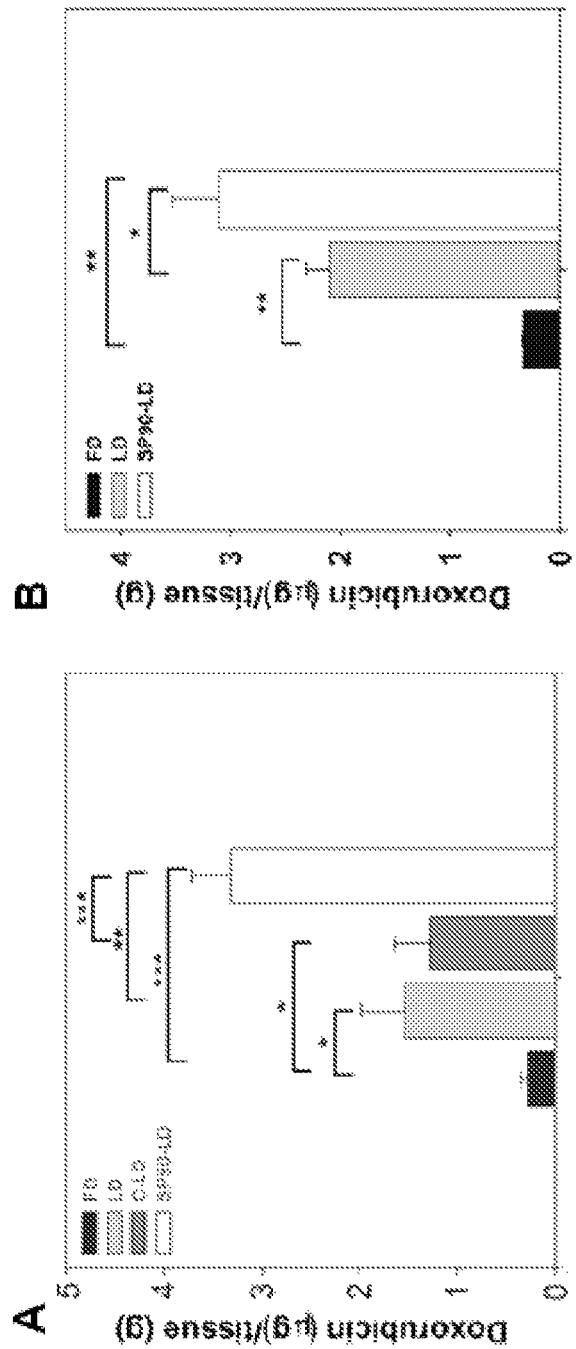
FIG. 4 is a diagram showing distribution of doxorubicin in tumor tissues. Panel A: with perfusion. Panel B: without perfusion.

The results obtained from this study, shown in FIG. 4, Panels A and B, indicated that the mean intra-tumor doxorubicin concentration in the SP90-LD-treated mice was 12.0 fold, 2.2 fold, and 2.6 fold higher than those in the FD-treated, LD-treated mice and mice treated with LD conjugated with a control peptide (C-LD), respectively. In addition, doxorubicin was detected in large areas in the tumor tissues in SP90-LD treated mice, while it was detected only in limited areas in the tumor tissues in LD, FD, or C-LD treated mice.

In sum, SP90 was found to be effective in facilitating targeted doxorubicin delivery to tumor tissues, resulting in tumor cell necrosis/apoptosis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated breast cancer-targeting peptide, comprising an amino acid sequence selected from the group consisting of:

QNIYAGVPMISF, (SEQ ID NO: 1)

EATNSHGSRTMG, (SEQ ID NO: 2)

TVSWSTTGRIPL, (SEQ ID NO: 3)

QLEFYTQLAHLI, (SEQ ID NO: 4)

and

SMDPFLFQLLQL. (SEQ ID NO: 5)

2. The peptide of claim 1, wherein the peptide consists of the amino acid sequence of SEQ ID NO:1, 2, 3, 4, or 5.

3. The peptide of claim 1, wherein the peptide includes the amino acid sequence of SEQ ID NO:5.

4. The peptide of claim 1, wherein the peptide consists of the amino acid sequence of SEQ ID NO:5.

5. An anti-cancer conjugate, comprising the breast cancer-targeting peptide of claim 1 and an anti-cancer drug.

6. The anti-cancer conjugate of claim 5, wherein the peptide consists of the amino acid sequence of SEQ ID NO:1, 2, 3, 4, or 5.

7. The anti-cancer conjugate of claim 6, wherein the peptide consists of the amino acid sequence of SEQ ID NO: 5.

8. The anti-cancer conjugate of claim 5, wherein the anti-cancer drug is encapsulated in a microparticle that is associated with the peptide.

9. The anti-cancer conjugate of claim 8, wherein the microparticle is a liposome.

10. The anti-cancer conjugate of claim 5, wherein the anti-cancer drug is selected from the group consisting of doxorubicin, tamoxifen, vinorelbine, vincristine, paclitaxel, lurtotecan, docetaxel, adriamycin, epirubicin, mitoxantrone, mitomycin, gemcitabine, cisplatin, oxaliplatin, vinblastine, 5-FU, UFUR, anastrozole, letrozole, exemestane.

11. The anti-cancer conjugate of claim 7, wherein the anti-cancer drug is encapsulated in a microparticle that is associated with the peptide.

12. The anti-cancer conjugate of claim 11, wherein the microparticle is a liposome.

13. The anti-cancer conjugate of claim 7, wherein the anti-cancer drug is selected from the group consisting of doxorubicin, tamoxifen, vinorelbine, vincristine, paclitaxel, lurtotecan, docetaxel, adriamycin, epirubicin, mitoxantrone, mitomycin, gemcitabine, cisplatin, oxaliplatin, vinblastine, 5-FU, UFUR, anastrozole, letrozole, exemestane.

14. A method of delivering an anti-cancer drug to a breast cancer site in a subject, comprising administering to a subject in need thereof the anti-cancer conjugate of claim 5.

15. The method of claim 14, wherein the breast cancer-targeting peptide consists of the amino acid sequence of SEQ ID NO:5.

16. An isolated nucleic acid, comprising a nucleotide sequence encoding the breast cancer-targeting peptide of claim 1.

17. The isolated nucleic acid of claim 16, comprising a nucleotide sequence encoding the sequence of SEQ ID NO:5.

* * * * *